(12) United States Patent
Koerber et al.

(10) Patent No.: US 11,351,326 B2
(45) Date of Patent: Jun. 7, 2022

(54) PORTABLE OXYGEN CONCENTRATION

(71) Applicant: KONINKLIJKE PHILIPS N.V., Eindhoven (NL)

(72) Inventors: Achim Gerhard Rolf Koerber, Eindhoven (NL); Rainer Hilbig, Aachen (DE); Brian Edward Dickerson, Canton, GA (US); Robert William Murdoch, Acworth, GA (US); Douglas Adam Whitcher, Oakmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 439 days.

(21) Appl. No.: 16/684,620

(22) Filed: Nov. 15, 2019

(65) Prior Publication Data
US 2020/0155785 A1 May 21, 2020

Related U.S. Application Data

(60) Provisional application No. 62/768,171, filed on Nov. 16, 2018.

(51) Int. Cl.
*A61M 16/10* (2006.01)
*A61M 16/20* (2006.01)

(52) U.S. Cl.
CPC ........ *A61M 16/101* (2014.02); *A61M 16/105* (2013.01); *A61M 16/202* (2014.02); *A61M 2202/0266* (2013.01); *A61M 2205/07* (2013.01); *A61M 2230/40* (2013.01)

(58) Field of Classification Search
CPC .............. A61M 16/10; A61M 16/1005; A61M 16/101; A61M 16/1015; A61M 2016/102; A61M 2016/1025; B01D 53/047
See application file for complete search history.

(56) References Cited

U.S. PATENT DOCUMENTS

| | | | |
|---|---|---|---|
| 5,529,607 A * | 6/1996 | Tan ..................... | B01D 53/047 95/138 |
| 5,917,135 A | 6/1999 | Michaels et al. | |
| 6,551,384 B1 | 4/2003 | Ackley et al. | |

(Continued)

FOREIGN PATENT DOCUMENTS

CN 108697872 A 10/2018

*Primary Examiner* — Joseph D. Boecker
*Assistant Examiner* — Thomas W Greig
(74) *Attorney, Agent, or Firm* — Daniel H. Brean

(57) ABSTRACT

The present disclosure describes a system and method for maintaining oxygen purity in portable oxygen concentrators, even with asymmetric generation of oxygen enriched gas volumes from different sieve beds of the concentration system. The present system and method compensate for asymmetric oxygen enriched gas generation using asymmetric delivery of purge volumes. Purge valves are used to deliver the asymmetric purge gas volumes, enables the system to maintain oxygen purity without additional power consumption, even when a portable oxygen concentrator does not include a product tank. The present system and method are configured such that asymmetry in enriched oxygen generation can be monitored and the asymmetric purge gas compensation can be applied independently from other control mechanisms of a portable oxygen concentrator.

15 Claims, 10 Drawing Sheets

(56) References Cited

U.S. PATENT DOCUMENTS

| | | | |
|---|---|---|---|
| 9,011,582 B2 * | 4/2015 | Ando | A61M 16/10 96/111 |
| 2006/0230929 A1 | 10/2006 | Bliss et al. | |
| 2009/0211448 A1 | 8/2009 | McClain | |
| 2014/0165830 A1 | 6/2014 | Dolensky | |
| 2016/0310886 A1 * | 10/2016 | Von Hollen | A61M 16/101 |
| 2018/0289992 A1 * | 10/2018 | Peake | A61M 16/101 |

* cited by examiner

PORTABLE OXYGEN CONCENTRATION

CROSS-REFERENCE TO RELATED APPLICATIONS

This patent application claims the priority benefit under 35 U.S.C. § 119(e) of Provisional Application No. 62/768,171 filed on Nov. 16, 2018, the contents of which are herein incorporated by reference.

BACKGROUND OF THE INVENTION

1. Field

The present disclosure pertains to a method and a portable system for concentrating oxygen.

2. Description of the Related Art

Oxygen therapy is known. Oxygen therapy benefits a patient by increasing the supply of oxygen to the lungs of the patient, thereby increasing the availability of oxygen to the body tissues of the patient. Oxygen therapy systems include portable, "on demand" oxygen therapy systems. For on demand generation of oxygen, commercial solutions such as oxygen concentrators have been developed. These oxygen concentrators use pressure swing adsorption (PSA) technology, which is described in U.S. Pat. No. 6,551,384, for example. A PSA process run by an on demand portable oxygen concentrator often causes asymmetric gas generation between sieve beds (e.g., one sieve bed produces more concentrated oxygen than another sieve bed), which can decrease the purity of oxygen gas generated by the system.

SUMMARY

It would be advantageous to achieve a portable oxygen concentration system configured to determine whether a volume of enriched gas produced by one sieve bed in a pair of sieve beds was different than a volume of enriched gas produced by the other sieve bed in the pair of sieve beds, and, determine different purge volumes of gas for the sieve beds based on the different volumes of enriched gas produced by the sieve beds.

Accordingly, one or more aspects of the present disclosure relate to a portable oxygen concentration system. The system comprises a pair of sieve beds, a pressure generator, one or more sensors, valves, one or more processors, and/or other components. The pressure generator is configured to generate pressurized gas that is directed through the sieve beds. The sieve beds output enriched gas for delivery to a subject in a pressure swing adsorption (PSA) process. The PSA process comprises alternating enriched gas production and purge cycles for each of the sieve beds such that when one of the sieve beds is alternating through an enriched gas production cycle, the other sieve bed is alternating through a purge cycle. The one or more sensors are configured to generate output signals conveying information related to respiration of the subject. The valves are configured to control gas flow into and out of the pair of sieve beds during the enriched gas production and purge cycles of the PSA process.

The one or more processors are configured by machine-readable instructions to cause the valves to control the gas flow into and out of the pair of sieve beds during the enriched gas production and purge cycles of the PSA process based on the output signals. The one or more processors are configured to determine whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds. Responsive to determining that the volume of enriched gas produced by one sieve bed in the pair of sieve beds is different than the volume of enriched gas produced by the other sieve bed in the pair of sieve beds, the one or more processors are configured to determine different purge volumes of gas for the sieve beds based on the different volumes of enriched gas produced by the sieve beds; and cause the valves to control the purge cycles of the PSA process based on the different purge volumes of gas determined for the sieve beds.

In some embodiments, the one or more processors are configured to cause the valves to control the purge cycles of the PSA process based on the different purge volumes of gas determined for the sieve beds to maintain a target purity of the enriched gas for delivery to the subject. In some embodiments, the one or more processors are configured such that causing the valves to control the purge cycles of the PSA process based on the different purge volumes of gas determined for the sieve beds comprises causing the valves to adjust purge times or flow rates of purge gas during the purge cycles of the PSA process.

In some embodiments, the one or more processors are configured such that determining whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds comprises: counting a number of enriched gas boluses delivered to the subject from each sieve bed, and comparing a count from each sieve bed to each other, or integrating enriched gas bolus flow rates over time for boluses delivered to the subject from each sieve bed to determine a total bolus volume delivered from each sieve bed, and comparing the total bolus volume from each sieve bed to each other.

In some embodiments, the one or more processors are configured such that causing the valves to control the purge cycles of the PSA process based on the different purge volumes of gas determined for the sieve beds comprises causing the valves to increase or decrease purge times or flow rates of purge gas for one or both sieve beds during the purge cycles of the PSA process such that whichever one of the pair of sieve beds output an increased volume of enriched gas relative to the other sieve bed receives an increased volume of enriched gas relative to the other sieve bed during a purge cycle.

In some embodiments, the one or more processors are further configured to determine whether an amount the volume of enriched gas produced by one sieve bed in the pair of sieve beds is different than the volume of enriched gas produced by the other sieve bed in the pair of sieve beds breaches a volume difference threshold. Responsive to determining that the amount the volume of enriched gas produced by one sieve bed in the pair of sieve beds is different than the volume of enriched gas produced by the other sieve bed in the pair of sieve beds breaches the volume difference threshold, the one or more processors are configured to determine the different purge volumes of gas for the sieve beds based on the different volumes of enriched gas produced by the sieve beds; and cause the valves to control the purge cycles of the PSA process based on the different purge volumes of gas determined for the sieve beds.

In some embodiments, the system does not include a product tank configured to store the enriched gas from the sieve beds.

It would be advantageous to achieve a method for determining whether a volume of enriched gas produced by one sieve bed in a pair of sieve beds was different than a volume of enriched gas produced by the other sieve bed in the pair of sieve beds, and, determining different purge volumes of gas for the sieve beds based on the different volumes of enriched gas produced by the sieve beds.

Accordingly, another aspect of the present disclosure relates to a method for concentrating oxygen with a portable oxygen concentration system. The system comprises a pair of sieve beds, a pressure generator, one or more sensors, one or more valves, one or more processors, and/or other components. The method comprises generating, with the pressure generator, pressurized gas that is directed through the sieve beds. The method comprises outputting enriched gas for delivery to a subject in a pressure swing adsorption (PSA) process. The PSA process comprises alternating enriched gas production and purge cycles for each of the sieve beds such that when one of the sieve beds is alternating through an enriched gas production cycle, the other sieve bed is alternating through a purge cycle. The method comprises generating, with the one or more sensors, output signals conveying information related to respiration of the subject. The method comprises controlling, with the valves, the gas flow into and out of the pair of sieve beds during the enriched gas production and purge cycles of the PSA process. The method comprises causing, with the one or more processors, the valves to control the gas flow into and out of the pair of sieve beds during the enriched gas production and purge cycles of the PSA process based on the output signals. The method comprises determining, with the one or more processors, whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds. The method comprises, responsive to determining that the volume of enriched gas produced by one sieve bed in the pair of sieve beds is different than the volume of enriched gas produced by the other sieve bed in the pair of sieve beds: determining, with the one or more processors, different purge volumes of gas for the sieve beds based on the different volumes of enriched gas produced by the sieve beds; and causing, with the one or more processors, the valves to control the purge cycles of the PSA process based on the different purge volumes of gas determined for the sieve beds.

In some embodiments, the method further comprises causing, with the one or more processors, the valves to control the purge cycles of the PSA process based on the different purge volumes of gas determined for the sieve beds to maintain a target purity of the enriched gas for delivery to the subject. In some embodiments, causing the valves to control the purge cycles of the PSA process based on the different purge volumes of gas determined for the sieve beds comprises causing the valves to adjust purge times or flow rates of purge gas during the purge cycles of the PSA process.

In some embodiments, determining whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds comprises: counting a number of enriched gas boluses delivered to the subject from each sieve bed, and comparing a count from each sieve bed to each other, or integrating enriched gas bolus flow rates over time for boluses delivered to the subject from each sieve bed to determine a total bolus volume delivered from each sieve bed, and comparing the total bolus volume from each sieve bed to each other.

In some embodiments, causing the valves to control the purge cycles of the PSA process based on the different purge volumes of gas determined for the sieve beds comprises causing the valves to increase or decrease purge times or flow rates of purge gas for one or both sieve beds during the purge cycles of the PSA process such that whichever one of the pair of sieve beds output an increased volume of enriched gas relative to the other sieve bed receives an increased volume of enriched gas relative to the other sieve bed during a purge cycle.

In some embodiments, the method further comprises determining, with the one or more processors, whether an amount the volume of enriched gas produced by one sieve bed in the pair of sieve beds is different than the volume of enriched gas produced by the other sieve bed in the pair of sieve beds breaches a volume difference threshold; and responsive to determining that the amount the volume of enriched gas produced by one sieve bed in the pair of sieve beds is different than the volume of enriched gas produced by the other sieve bed in the pair of sieve beds breaches the volume difference threshold: determining, with the one or more processors, the different purge volumes of gas for the sieve beds based on the different volumes of enriched gas produced by the sieve beds; and causing, with the one or more processors, the valves to control the purge cycles of the PSA process based on the different purge volumes of gas determined for the sieve beds.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1A:
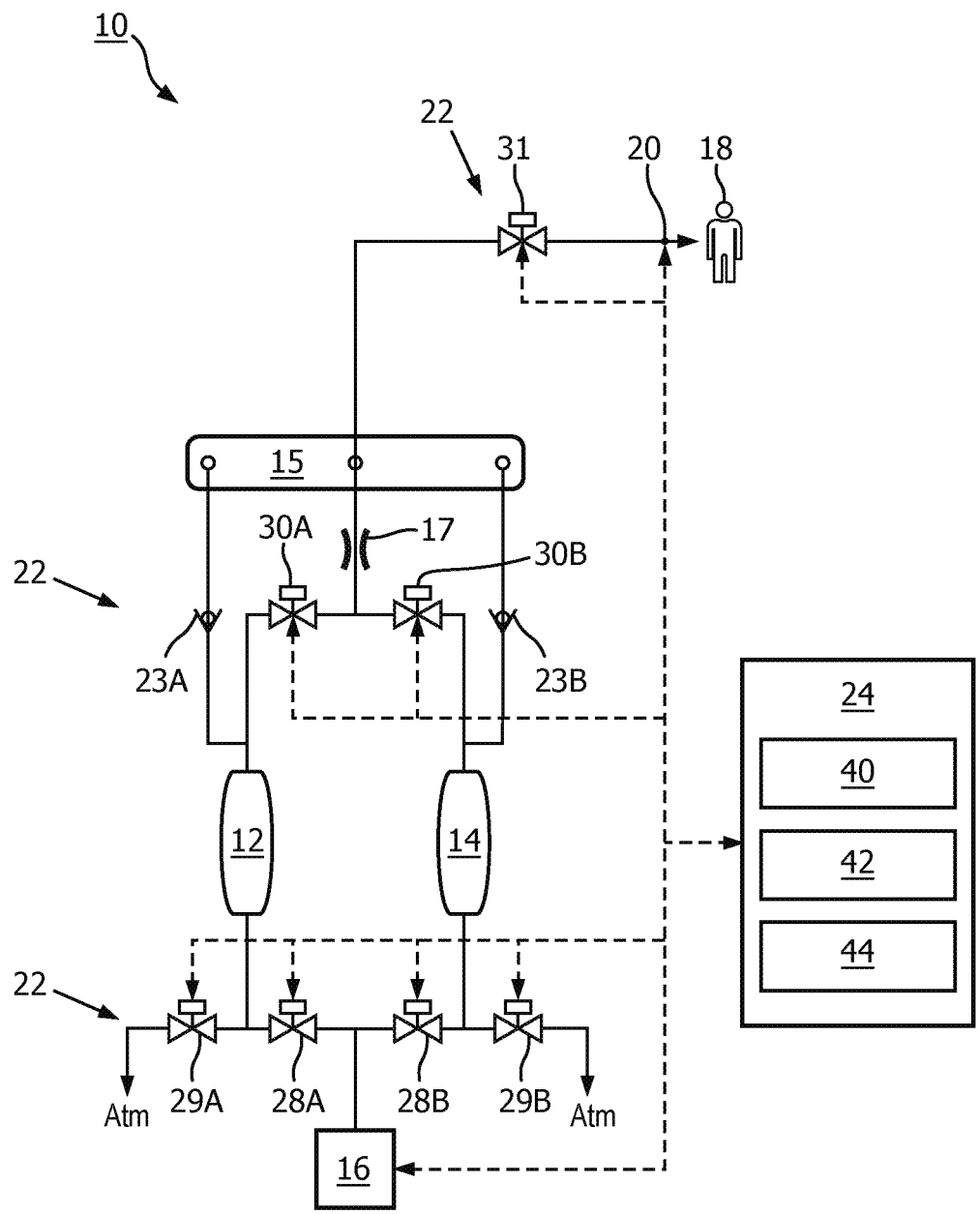
FIG. 1A is a first schematic illustration of a portable system for concentrating oxygen, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1A-1D are schematic illustrations of a portable system 10 for concentrating oxygen, in accordance with one or more embodiments. System 10 comprises a pair of sieve beds 12 and 14, a pressure generator 16, one or more sensors 20, one or more valves 22, one or more physical computer processors 24, and/or other components. Generally, oxygen may be purified from air in an oxygen concentrator by a process called Pressure Swing Adsorption (PSA). Sieve beds 12 and 14 comprise two tubes (and/or other structures) filled with a molecular sieve material (e.g., Zeolite and/or other materials). This material is configured to preferentially adsorb nitrogen over oxygen or argon. This attribute can be used to produce oxygen and/or argon enriched product gas stream when pressurized air flows through one of the molecular sieve beds by removing a majority of the nitrogen molecules from the stream. A single molecular sieve tube (e.g., sieve bed 12 or 14) has a finite nitrogen adsorption capacity at any fixed pressure and temperature before nitrogen adsorption equilibrium is reached, and nitrogen may start breaking through an oxygen outlet of a sieve bed (e.g., sieve bed 12) if that adsorption capacity is reached. System 10 is configured such that shortly before this point is reached, oxygen production switches to the second sieve bed (e.g., sieve bed 14) while the first sieve bed 12 exhausts its pressure, is purged with purge gas, and regenerates to equilibrium at ambient conditions. This process continues back and forth between the two sieve beds 12 and 14 to supply a flow of enriched oxygen gas to a subject 18 as the oxygen is demanded by subject 18.

Generally, a PSA cycle involves five steps. These steps include pressurization, oxygen production, balance, blowdown (exhaust), and purge. Below is a description of these steps starting with pressurization of sieve bed 12.

Pressurization: Pressure generator 16 feeds pressurized gas (e.g., air) to sieve bed 12 through an open feed valve 28A as shown in FIGS. 1A and 1C (or through a three way combination feed/exhaust valve 28/29A shown in FIGS. 1B and 1D), increasing the pressure of sieve bed 12, resulting in nitrogen (for example) being adsorbed out of the gas flow, and outputting a purified oxygen flow from sieve bed 12.

Pressure generator 16 is configured to generate a pressurized gas for delivery to sieve beds 12 and 14. Pressure generator 16 receives a flow of gas from a gas source, such as the ambient atmosphere, and elevates the pressure of that gas for delivery to sieve beds 12 and 14. Pressure generator 16 is any device, such as, for example, a compressor, a pump, blower, piston, or bellows, that is capable of elevating the pressure of the received gas. Pressure generator 16 may comprise one or more valves for controlling the pressure and/or flow of gas, for example. The present disclosure also contemplates controlling the operating speed of a blower, either alone or in combination with such valves, to control the pressure and/or flow of gas provided to sieve beds 12 and 14.

Figure 1B:
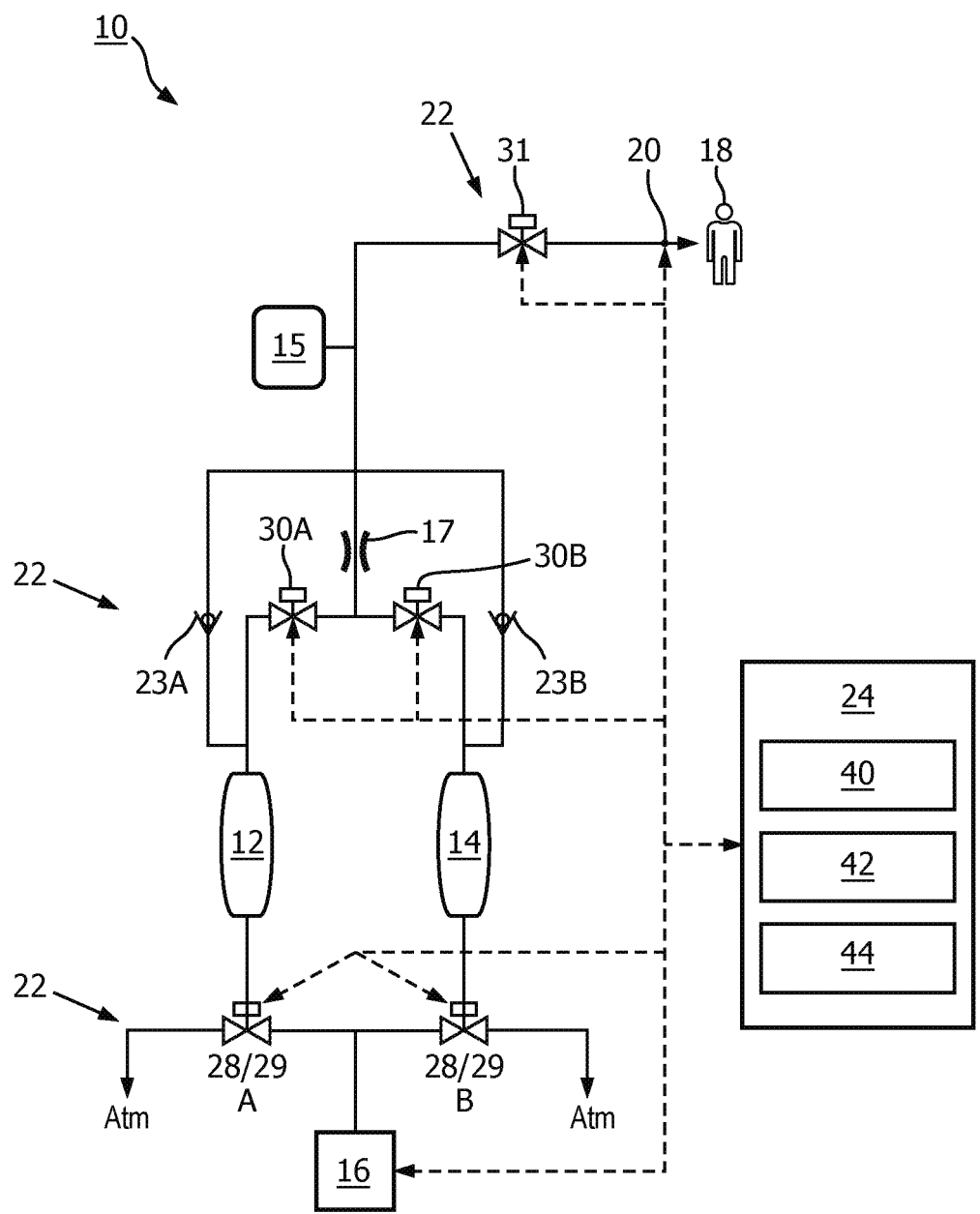
FIG. 1B is a second schematic illustration of a portable system for concentrating oxygen, in accordance with one or more embodiments.
Figure 1C:
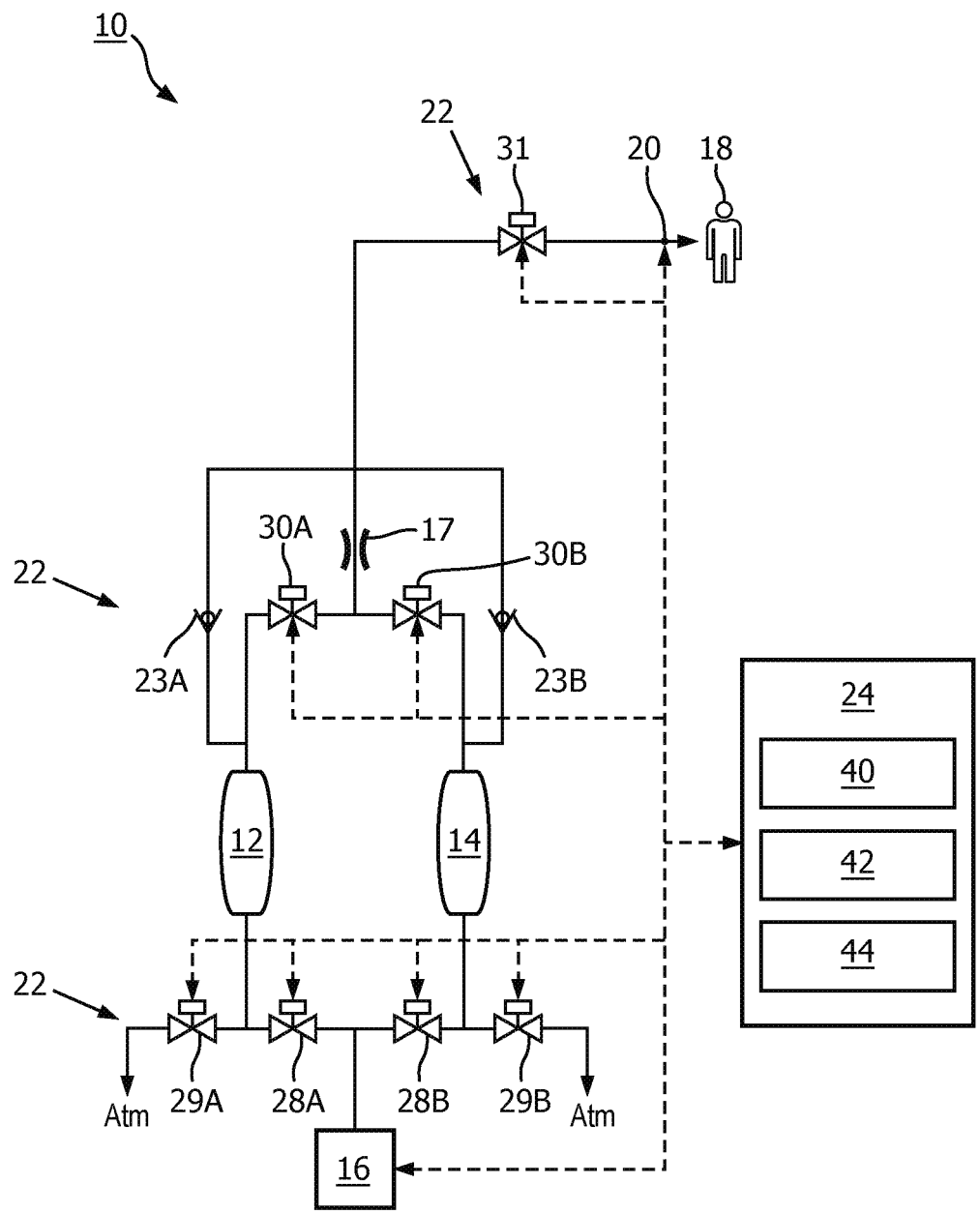
FIG. 1C is a third schematic illustration of a portable system for concentrating oxygen, in accordance with one or more embodiments.
Figure 1D:
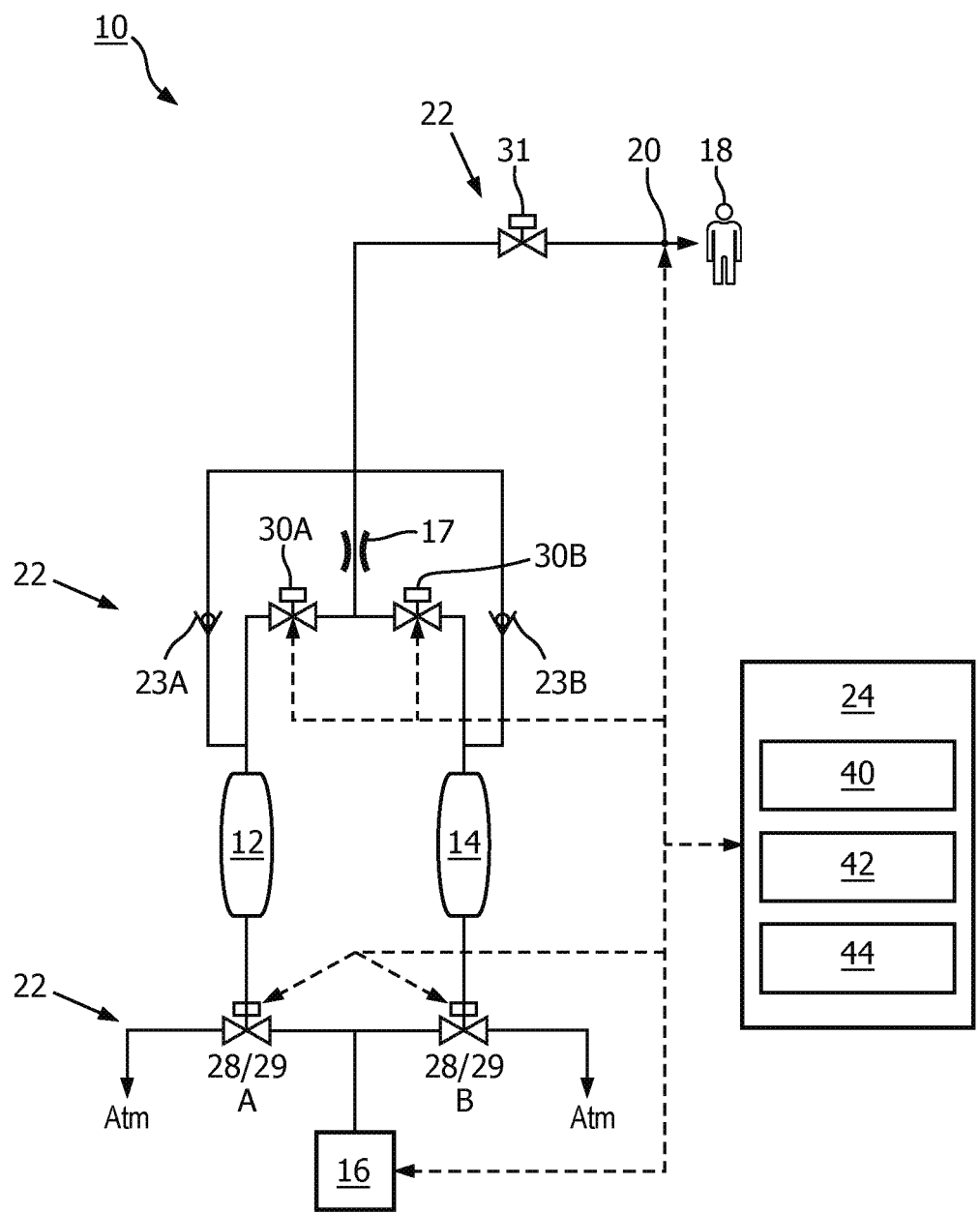
FIG. 1D is a fourth schematic illustration of a portable system for concentrating oxygen, in accordance with one or more embodiments.

As shown in FIG. 1A-1D, valves 22 include check valves 23A and 23B, feed valves 28A and 28B, and exhaust valves 29A and 29B (e.g., as illustrated in FIGS. 1A and 1C); three way combination feed/exhaust valves 28/29A and 28/29B (e.g., as shown in FIGS. 1B and 1D); purge valves 30A and 30B (e.g., as shown in FIG. 1A-1D); and/or other valves. Valves 22 are configured to selectively control flow through system 10. Valves 22 may be closed, or closed in a specific direction, such that substantially no gas is communicated therethrough; or opened (or partially open) to permit gas flow. In some embodiments, valves 22 may comprise one or more of a plug valve, a ball valve, a check valve, a butterfly valve, a solenoid, a pneumatical pilot operated valve, and/or other valves. Valves 22 may be controlled electronically (e.g., by processor 24), hydraulically, pneumatically, via an electric motor, any combination of the above control mechanisms, and/or another mode of control configured to open and/or close a valve.

When the increased pressure in sieve bed 12 surpasses the pressure of the oxygen gas stored in (optional) product tank 15 (e.g., as shown in FIGS. 1A and 1B, but not shown in FIG. 1C or 1D) and/or other system components downstream from sieve bed 12, check valve 23A opens. Exhaust valve 29A (or an exhaust direction of feed/exhaust valve 28/29A shown in FIGS. 1B and 1D) used to vent gas pressure from sieve bed 12 is closed, feed valve 28B as shown in FIGS. 1A and 1C (or a three way combination feed/exhaust valve 28/29B shown in FIGS. 1B and 1D) is closed, check valve 23B is closed (e.g., due to sieve bed 14 having low pressure), and exhaust valve 29B (or the exhaust direction of feed/exhaust valve 28/29B shown in FIGS. 1B and 1D) used to vent air pressure from sieve bed 14 is open.

Oxygen Production: Pressure generator 16 continues feeding gas (e.g., air) to sieve bed 12, which pushes the enriched (e.g., oxygen) gas through open check valve 23A into (optional) product tank 15. In some embodiments, product tank 15 is a gas storage tank used as a pressure buffer to help provide a relatively steady source of enriched oxygen gas to deliver to subject 18. However, as described below, product tank 15 is only an optional part of system 10 and the control mechanisms described below reduce or eliminate a need for product tank 15. The oxygen production step ends before nitrogen gas breaks through and flows into product tank 15, lowering the purity of the stored oxygen to be supplied to the patient.

Balance: At the end of the oxygen production step, sieve bed 12 is pressurized to near its maximum cycle pressure, and sieve bed 14 is near atmospheric pressure. Dumping the pressurized gas in sieve bed 12 to atmosphere may waste energy because system 10 would be required to pressurize more ambient air than necessary in the next step. To recover some of this energy, exhaust valve 29B (FIGS. 1A and 1C) is closed (or three way combination valve 28/29 (FIGS. 1B and 1D) is appropriately positioned) and purge valves 30A and/or 30B (FIGS. 1B and 1D) are open at the oxygen outlets of sieve beds 12 and 14 for a short time to equalize the pressure between the two beds. In this way, less energy is required to pressurize new air in sieve bed 14. During the balance step, the gas (e.g., air) feed from pressure generator 16 is switched from flowing through feed valve 28A (or three way valve 28/29A) to flow through feed valve 28B (or three way valve 28/29B). In some embodiments, there may be an additional balance valve located parallel to the series of the two purge valves 30A and 30B. This valve would be opened during balancing only and would serve to provide a higher gas flow than the series of the two purge valves 30A and 30B would permit.

Blowdown: To dump the remaining pressurized gas from sieve bed 12 to atmosphere, allowing the sieve material of sieve bed 12 to desorb the excess nitrogen in sieve bed 12, exhaust valve 29A (FIGS. 1A and 1C) is opened (or three way valve 28/29A (FIGS. 1B and 1D) is positioned to exhaust gas to atmosphere).

Purge: When the pressure in one sieve bed (12 or 14) is lower than the pressure in the other sieve bed (12 or 14), a flow of oxygen enriched gas flows from the oxygen outlet of the higher pressure bed through the purge orifice 17 and purge valve 30A or 30B into the oxygen outlet of the lower pressure bed being vented to purge excess nitrogen gas from that bed to atmosphere. Continuing with this example, sieve bed 12 is purged using enriched oxygen flowing from sieve bed 14. The purge step is used to clean sieve bed 12 of excess nitrogen that would re-adsorb, reducing the air separation capacity of the following cycle. One can also consider the purge step as a phase when additional oxygen product gas is stored into the sieve bed to be purged 12.

The two sieve beds work in tandem with one bed being in the pressurization and/or oxygen production side of the cycle, while the other bed is in the blowdown and/or purge side of the cycle. During the next half cycle the two beds switch steps to continue to produce enriched (e.g., oxygen) gas. In some embodiments, check valve 23A may be used to allow enriched gas generated from sieve bed 12 to flow into product tank 15 (FIGS. 1A and 1B), or simply downstream from sieve bed 12 (FIGS. 1C and 1D), whenever the pressure of sieve bed 12 exceeds the pressure in product tank 15, or the pressure in system 10 downstream form sieve bed 12. In some embodiments, check valve 23B may be used to allow enriched gas generated from sieve bed 14 to flow into product tank 15 (FIGS. 1A and 1B), or simply downstream from sieve bed 14 (FIGS. 1C and 1D), whenever the pressure of sieve bed 14 exceeds the pressure in product tank 15, or the pressure in system 10 downstream form sieve bed 14.

In some embodiments, system 10 may include a patient delivery valve 31. In a Portable Oxygen Concentrator (POC), patient delivery valve 31 may be a direct acting solenoid valve and/or other valves controlled by a patient breath detection circuit (e.g., sensor 20 and processor 24 described below) to deliver a specified pulsed bolus volume of enriched gas at the initiation of each breath of subject 18.

Summarizing, an oxygen concentration system 10 with active purge valves 30A and 30B is shown in FIG. 1A-1D. System 10 may include separate feed and exhaust valves (FIGS. 1A and 1C) or combination three way valves (FIGS. 1B and 1D) at the feed side of the two sieve beds 12 and 14. Oxygen is fed from the product side of the sieve beds 12 and 14 via check valves 23A and 23B into the optional oxygen tank 15. Oxygen tank 15 (if present) may provide oxygen back into a sieve bed 12 or 14 via purge orifice 17 and a purge valve 30A or 30B respectively. At the end of an individual half cycle the pressure difference between the sieve beds 12 and 14 may be equalized by opening both purge valves 30A and 30B simultaneously and/or opening an optional balancing valve as described herein and/or switching both three-way air side process valves (28/29A and 28/29B in FIGS. 1B & 1D) simultaneously into their air feed positions.

In some embodiments, system 10 includes switchable ("active") purge valves 30A and 30B in series with a stationary purge orifice 17 connecting the sieve beds 12 and 14 because this arrangement facilitates adapting the purge volume to a range of product output flows and/or other operations.

In order to save energy, size, and weight, for example, a portable oxygen concentrator (POC) system such as system 10 may not deliver a continuous flow of oxygen to subject 18 because the oxygen delivered during the exhalation phase of subject 18 would not be inhaled, and would thus be wasted. Instead, a POC such as system 10 uses a sensor (e.g., sensor 20 described below) to detect the start of the inhalation phase of subject 18, and then delivers a defined pulse volume ("bolus") of gas (e.g., oxygen) to subject 18. A bolus is delivered when the patient inhales, not at a specific time predetermined by system 10.

On demand bolus delivery as described above often produces an asymmetric loading condition. An asymmetric loading condition occurs when the oxygen volumes VA and VB delivered by sieve bed 12 and 14 per unit time are not equal. If an asymmetric load condition continues and no countermeasures are taken (e.g., such as the countermeasures described herein), there is normally a (significant) decrease in gas (e.g., oxygen) purity in the boli delivered to subject 18. The decrease in gas purity is caused by nitrogen breakthrough in sieve bed 12 or 14, whichever one delivered the larger volume of gas to subject 18.

As an example, assume the cycle time of system 10 is $t_{cyc}=9$ s (having a half-cycle time of 4.5 s) and subject 18 is breathing at a constant breathing rate of BR=20 breaths/min. In this example, system 10 has to deliver $BR*t_{cyc}=3$ boli per cycle. This means that two boli would be delivered by sieve bed 12 (for example) in one half-cycle, and one bolus would be delivered by sieve bed 14 in the other half-cycle. Without corrective action, these example conditions would likely lead to nitrogen breakthrough in sieve bed 12, and consequently to a drop in oxygen (for example) purity of the gas (e.g., 90%→<83%) delivered to subject 18 within a matter of minutes.

Figure 2:
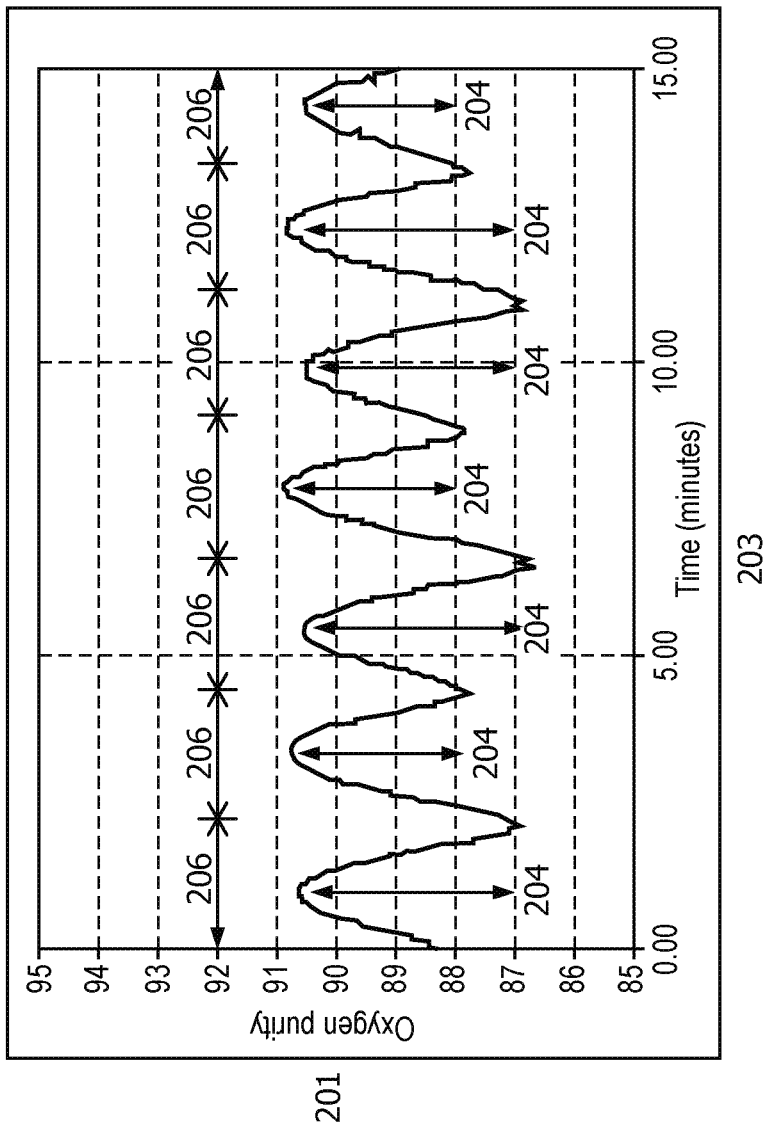
FIG. 2 illustrates recorded purity measurements over time for a typical system at a typical bolus delivery rate, in accordance with one or more embodiments.

FIG. 2 illustrates recorded purity 201 measurements 204 over time 203 for a typical system at a bolus delivery rate of $(BR*t_{cyc}=)$ 3.03 boli per cycle (e.g., slightly more than the rate of 3 boli per cycle in the hypothetical example described above). The system used to generate the information shown in FIG. 2 was a portable oxygen concentrator arranged as described above (e.g., with a breathing rate of 20 breaths/minute, a motor speed of 2325 RPM, a feed time of 4.55 seconds, a balance time of 0.4 seconds, a purge time of 2.75 seconds, and a purge orifice having a 0.02 inch diameter). As shown in FIG. 2, the purity 201 of oxygen delivered by such a system (without the corrective operations described herein) oscillates 204 over a half-period 206 of only several minutes.

Figure 3:
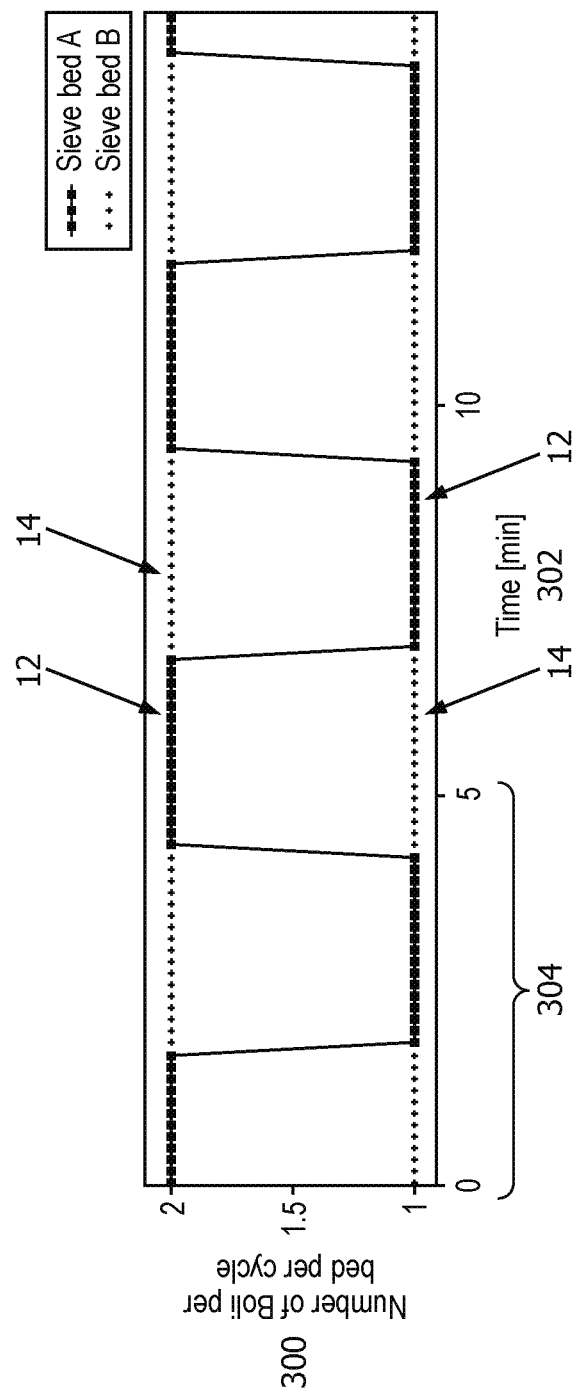
FIG. 3 illustrates a simulation of the number of boli delivered per sieve bed per cycle under asymmetric load conditions, in accordance with one or more embodiments.

This purity oscillation occurs over time because both sieve beds (12 and 14 shown in FIG. 1A-1D), under the example conditions described above, alternate as the sieve bed delivering more oxygen during a certain number of cycles (e.g., 16.5 cycles bed 12, 16.5 cycles bed 14). This is illustrated in FIG. 3. FIG. 3 illustrates a simulation of the number of boli delivered per sieve bed per cycle under asymmetric load conditions. The conditions used for asymmetric load conditions in FIG. 3 are those discussed above related to FIG. 2: $BR*t_{cyc}$=3.03 pulses/cycle. As shown in FIG. 3, sieve bed 12 and sieve bed 14 alternate as the sieve bed that produces more boli 300 over time 302. This is shown by the lines that represent sieve beds 12 and 14 alternating between 2 boli per bed per cycle and 1 bolus per bed per cycle at opposite times 302. The theoretical repetition period 304 in this example is 4.95 min.

In some embodiments (e.g., as shown in FIGS. 1A and 1B), system 10 may include product tank 15 to dampen this effect. However, inclusion of product tank 15 may increase a size and weight of system 10. In some embodiments, system 10 may be configured to dampen this effect by adapting the cycle time $t_{cyc}$ so that system 10 is at least several percent away from known critical cycle time values (e.g., $BR*t_{cyc}$=1, 3, 5, . . . ) that cause one sieve bed to deliver more boli than the other sieve bed. For these critical cycle time values the number of boli per bed per cycle would be 1/0, 2/1, 3/2, . . . . However, there may be more asymmetric points than those few characterized by odd numbers. This is illustrated in FIG. 4.

Figure 4:
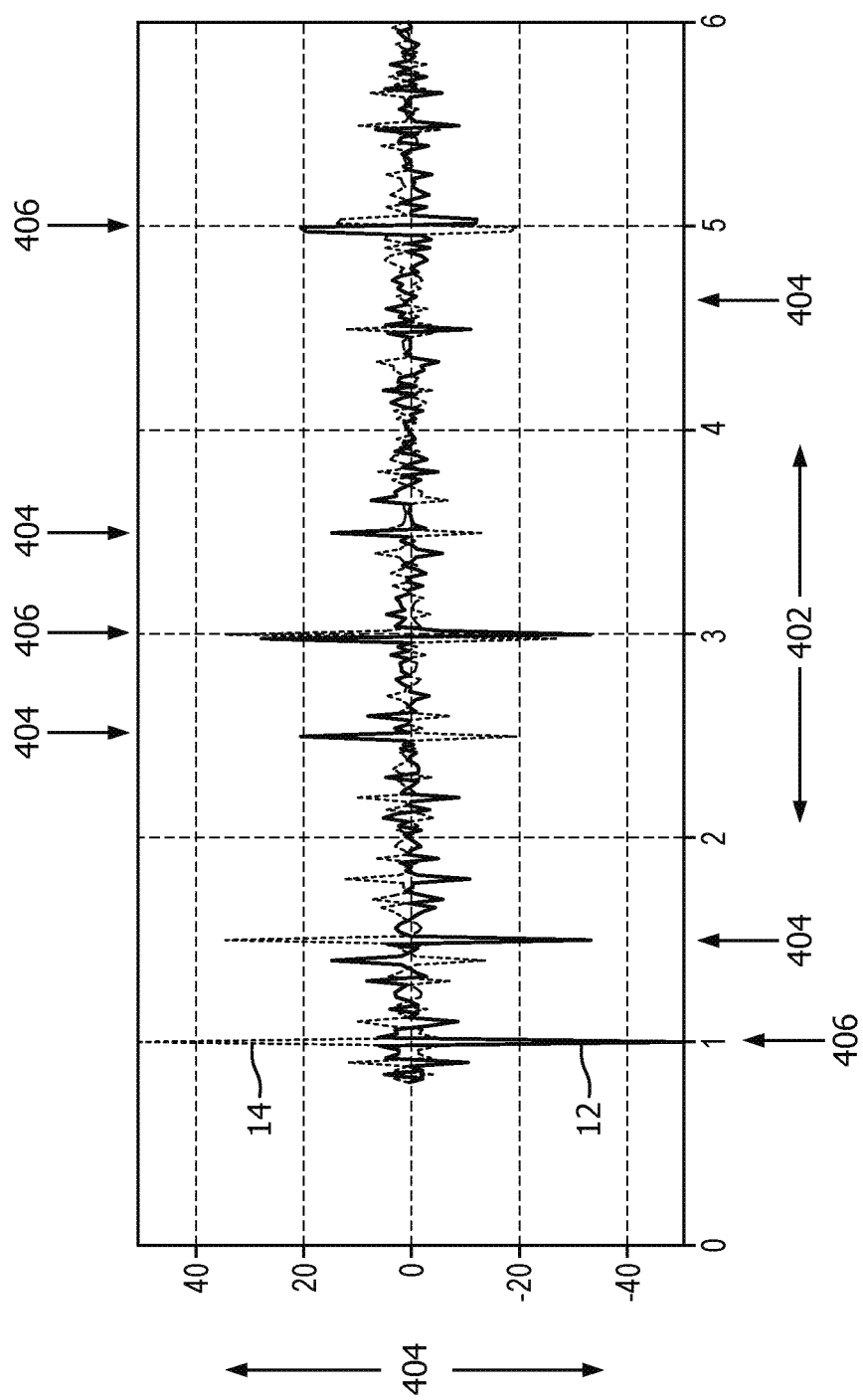
FIG. 4 illustrates asymmetric loading of two sieve beds, in accordance with one or more embodiments.

FIG. 4 illustrates asymmetric loading of sieve bed 12 and sieve bed 14. FIG. 4 illustrates the relative excess or deficiency of oxygen (as a percentage) per cycle 400 as the number of boli ($BR*t_{cyc}$) 402 increases. As shown in FIG. 4, there are more asymmetric points 404 than just those 406 at odd numbers of boli. As an example, the indicated asymmetric points 404 are corresponding to $BR*t_{cyc}$=1.5, 2.5, 3.5 and 4.5. These are situations where the number of boli per bed per cycle are 1/0.5 (i.e. the second bed would provide a bolus only every second cycle), 1.5/1, 2/1.5 and 2.5/2, respectively.

Returning to FIG. 1A-1D, instead of (and/or in addition to) including product tank 15 or adapting the cycle time to be at least several percent away from known critical values, system 10 may be configured to control active purge valves 30A and 30B to compensate for an asymmetric load condition with asymmetric purge volumes. For example, system 10 is configured such that the sieve bed (e.g., either sieve bed 12 or 14) which has delivered an excess gas (e.g., oxygen) volume during its producing half-cycle will receive back a corresponding excess volume of oxygen during its purge phase. In this way, the position of a mass transfer zone in that particular sieve bed is stabilized, and the positions of the mass transfer zones stay symmetrical for both sieve beds, even under asymmetric load conditions (e.g., $BR*t_{cyc}$=1), even, as an extreme example, where one sieve bed delivers all (oxygen) boli.

System 10 is configured to control (e.g., oxygen) purity in situations that would normally cause variations of purity on a minute scale. As described above, system 10 includes active (switchable) purge valves 30A and 30B (e.g. electrically operated solenoidal valves and/or other valves as described above) configured to facilitate compensation for asymmetric product volumes from the sieve beds 12 and 14 by a successive asymmetric delivery of purge volumes from one sieve bed to the other. Advantageously, this results in stable oxygen purity delivered by system 10 without a need for additional power or a product tank. Asymmetric purge gas volume control may be applicable in many and/or all load conditions (e.g., even if subject 18 breathes completely irregularly). Asymmetric purge gas volume control may be applied independently of other control algorithms involving the traditional sensor signals (e.g., sieve bed pressure curves, product $O_2$ content) and system parameters (e.g., half-cycle times, equalization times, compressor RPM). In fact, system 10 may perform the operations described herein as first steps before traditional control algorithms are applied. In this way, the efficiency of POC operation is enhanced, because traditional control algorithms often compensate for a drop in oxygen product purity on a minute scale by increasing the compressor RPM (e.g., requiring a corresponding increase in the device input power).

Returning to the components of system 10 shown in FIG. 1A-1D, sensor 20 is configured to generate one or more output signals conveying information related to respiration of subject 18. In some embodiments, the information related to respiration of subject 18 may be and/or include one or more gas parameters of the gas in system 10, respiration parameters of subject 18, and/or other information. In some embodiments, system 10 is configured to sense the start of inhalation based on a pressure drop in a cannula line that provides gas to subject 18.

Sensors 20 may comprise one or more sensors that generate output signals that convey information related to respiration in subject 18 directly and/or indirectly. For example, one or more sensors 20 may generate an output signal directly based on a flow of gas caused by respiration of subject 18, indirectly based on a heart rate of subject 18 (e.g., sensors 20 may be and/or include a heart rate sensor located on the chest of subject 18, and/or be configured as a bracelet on a wrist of subject 18, and/or be located on another limb of subject 18), movement of subject 18 (e.g., sensors 20 may include a bracelet around the wrist and/or ankle of subject 18 with an accelerometer such that respiration may be analyzed using actigraphy signals), and/or other characteristics of subject 18. Although sensors 20 are illustrated at a single location in a flow path of system 10 proximate to subject 18, this is not intended to be limiting. Sensors 20 may include sensors disposed in a plurality of locations, such as for example, within (or in communication with) a cannula that delivers gas to subject 12, a mask or other interface device worn by subject 18, coupled (in a removable manner) with clothing of subject 18, worn by subject 18 as a headband, wristband, etc.), positioned to point at subject 18 (e.g., a camera that conveys output signals related to chest movement of subject 18), and/or in other locations.

Processor 24 is configured to provide information-processing capabilities in system 10. As such, processor 24 may comprise one or more of a digital processor, an analog processor, a digital circuit designed to process information, an analog circuit designed to process information, a state machine, and/or other mechanisms for electronically processing information. Although processor 24 is shown in FIG. 1A-1D as a single entity, this is for illustrative purposes only. In some embodiments, processor 24 may comprise a plurality of processing units. These processing units may be physically located within the same device (e.g., a portable oxygen concentration system), or processor 24 may represent processing functionality of a plurality of devices operating in coordination. In some embodiments, processor 24 may be and/or be included in a computing device such as a desktop computer, a laptop computer, a smartphone, a tablet computer, a server, and/or other computing devices associated with system 10. Such computing devices may run one or more electronic applications having graphical user interfaces configured to facilitate user interaction with system 10.

As shown in FIG. 1A-1D, processor 24 is configured to execute one or more computer program components. The computer program components may comprise software programs and/or algorithms coded and/or otherwise embedded in processor 24, for example. The one or more computer program components may comprise one or more of a control component 40, an asymmetry component 42, an adjustment component 44, and/or other components. Processor 24 may be configured to execute components 40, 42, and/or 44 by software; hardware; firmware; some combination of software, hardware, and/or firmware; and/or other mechanisms for configuring processing capabilities on processor 24.

It should be appreciated that although components 40, 42, and 44 are illustrated in FIG. 1A-1D as being co-located within a single processing unit, in embodiments in which processor 24 comprises multiple processing units, one or more of components 40, 42, and/or 44 may be located remotely from the other components. The description of the functionality provided by the different components 40, 42, and/or 44 described below is for illustrative purposes, and is not intended to be limiting, as any of components 40, 42, and/or 44 may provide more or less functionality than is described. For example, one or more of components 40, 42, and/or 44 may be eliminated, and some or all of its functionality may be provided by other components 40, 42, and/or 44. As another example, processor 24 may be configured to execute one or more additional components that may perform some or all of the functionality attributed below to one of components 40, 42, and/or 44.

Control component 40 is configured to control gas flow into and out of sieve beds 12 and 14 during the enriched gas production and purge cycles of the PSA process. Control component 40 is configured to cause valves 22 to control the gas flow into and out of sieve beds 12 and 14 during the enriched gas production and purge cycles of the PSA process based on the output signals from sensor(s) 20 and/or other information. In some embodiments, control component 40 is configured to control gas flow based on one or more respiration parameters described above that indicate a start of inhalation or other respiratory effort in subject 18. For example, control component 40 may control one or more valves 22 to ensure enriched oxygen is supplied to subject 18 on demand. Continuing with this example, control component 40 may be configured to cause purge valves 30A and 30B to control gas flow into and out of sieve beds 12 and 14 during the corresponding purge cycles of the PSA process.

Asymmetry component 42 is configured to determine whether a volume of enriched gas produced by one sieve bed (e.g., sieve bed 12) in the pair of sieve beds is different than a volume of enriched gas produced by the other sieve bed (e.g., sieve bed 14) in the pair of sieve beds. Asymmetry component 42 is configured to determine whether causing valves 22 to control the gas flow into and out of sieve beds 12 and 14 based on the output signals caused a volume of enriched gas produced by one sieve bed (e.g., sieve bed 12) in the pair of sieve beds to be different than a volume of enriched gas produced by the other sieve bed (e.g., sieve bed 14) in the pair of sieve beds.

In some embodiments, determining whether causing valves 22 to control the gas flow into and out of the pair of sieve beds 12 and 14 based on the output signals caused a volume of enriched gas produced by one sieve bed in the pair of sieve beds to be different than a volume of enriched gas produced by the other sieve bed in the pair of sieve beds comprises: (1) counting a number of enriched gas boluses delivered to the subject from each sieve bed, and comparing a count from each sieve bed to each other, or (2) integrating enriched gas bolus flow rates over time for boluses delivered to the subject from each sieve bed to determine a total bolus volume delivered from each sieve bed, and (3) comparing the total bolus volume from each sieve bed to each other. In some embodiments, asymmetry component 42 is configured to determine the gas (e.g., oxygen) product volumes VA and VB supplied by each sieve bed (12 and 14) in one PSA cycle and determine the difference $\Delta V = VA - VB$.

Expanding on the paragraph above, if control component 40 is controlling the other components of system 10 to keep a bolus volume (VP) constant, asymmetry component 42 is configured to count the number of boli delivered by each sieve bed 12 and 14 in one PSA cycle (NA, NB), and multiply the number of boli from each side with the corresponding bolus volume (Option (1) in the paragraph above): $VA = NA*VP$, $VB = NB*VP$, which gives $\Delta V = VA - VB = (NA - NB)*VP$. If the delivered bolus volumes are not constant (Option (2) in the paragraph above), asymmetry component 42 is configured to integrate the gas (e.g., $O_2$) product flow rate within one bolus, $\Phi P(t)$, over the bolus delivery time to yield individual bolus volumes, $VP_i$, which are summed over one PSA cycle to obtain VA and VB, respectively. The term $\Phi P(t)$ is, for example, determined based on a measurement of a pressure differential $\Delta p(t)$ across a known (e.g., 02) path resistance. This may be, for example, product delivery valve 31, because our experimental fits of the dependence of $\Phi P(t)$ on $\Delta p(t)$ yielded that $\Phi P(t)$ is proportional to $\Delta p(t)^{0.537}$.

In some embodiments, asymmetry component 42 is configured to determine whether an amount the volume of enriched gas produced by one sieve bed in the pair of sieve beds 12 and 14 is different than the volume of enriched gas produced by the other sieve bed in the pair of sieve beds 12 and 14 breaches a volume difference threshold. The volume difference threshold may be determined by asymmetry component 42 based on information from previous therapy sessions for subject 18 or users demographically similar to subject 18, may be determined at manufacture of system 10, may be entered and/or selected via a user interface of system 10 by subject 18 and/or other users, and/or may be determined in other ways.

Adjustment component 44 is configured to, responsive to a determination by asymmetry component 42 that the volume of enriched gas produced by the sieve beds 12 and 14 is different (e.g., the volume of enriched gas produced by one sieve bed (e.g., sieve bed 12) in the pair of sieve beds is different than the volume of enriched gas produced by the other sieve bed (e.g., sieve bed 14) in the pair of sieve beds), or different by more than a threshold amount, determine different purge volumes of gas for the different sieve beds 12 and 14. This includes determining different purge volumes of gas for sieve beds 12 and 14 based on the different volumes of enriched gas produced by sieve beds 12 and 14.

For example, adjustment component 44 may be configured to determine, for a next PSA cycle, an adjustment for the O$_2$ purge volumes received by bed 12 (VpA) and received by bed 14 (VpB) such that VpA−VpB=(VA−VB)/2. In this way the net delivered amounts of O$_2$, nVA=VA−VpA+VpB, and nVB=VB−VpB+VpA, are identical (or nearly identical) (e.g., both are equal to ½*(VA+VB)) and the conditions within sieve beds 12 and 14 may remain as symmetrical as possible. It is important to realize that the net delivered amount of 02 (e.g., nVA) is made up of three terms: the delivered product VA, the received purge from B−VpA, and the purge delivered to B+VpB. Omission of the third term, for example, would lead to a purge compensation that would be a factor of two too high.

Control component 40 is configured such that the purge cycles of the PSA process are controlled based on the different purge volumes determined by adjustment component 44 for sieve beds 12 and 14. In some embodiments, control component 40 is configured to cause valves 22 to control the purge cycles of the PSA process based on the different purge volumes of gas determined for sieve beds 12 and 14 by causing valves 22 (e.g., purge valves 30A and 30B) to adjust purge times or flow rates of purge gas during the purge cycles of the PSA process.

In some embodiments, causing the valves to control the purge cycles of the PSA process based on the different purge volumes of gas determined for the sieve beds comprises causing the valves to increase or decrease purge times or flow rates of purge gas for one or both sieve beds during the purge cycles of the PSA process such that whichever one of the pair of sieve beds output an increased volume of enriched gas relative to the other sieve bed receives an increased volume of enriched gas relative to the other sieve bed during a purge cycle.

For example, in some embodiments, control component 40 is configured to adjust the purge volume of only one sieve bed, either by increasing VpA by +(VA−VB)/2, or by decreasing VpB by −(VA−VB)/2. Advantageously, this single purge adjustment compensation involves adjustment of only one parameter (e.g., the purge volume of one sieve bed). In some embodiments, control component 40 is configured for dual purge adjustment compensation. In these embodiments, control component 40 may increase VpA by +(VA−VB)/4, and at the same time decrease VpB by −(VA−VB)/4. Dual purge adjustment compensation involves the adjustment of at least two parameters (e.g., the purge volumes of both sieve beds 12 and 14), but has the advantage that the magnitude of the required changes ((VA−VB)/4) are half the magnitude of the changes ((VA−VB)/2) required for single purge adjustment compensation. Advantageously, with dual purge adjustment compensation, a broader range of asymmetries may be corrected within a given range of other control parameter values.

The purge volume, Vp, is the product of purge flow rate, Φp, and purge time, Δtp, such that Vp=Φp*tp. As described above, control component 40 may adjust the purge volumes, VpA and/or VpB, by either adjusting (e.g., increasing or decreasing) the purge flow rate, Φp, or the purge time, tp (or both) for one or both sieve beds 12 and 14 during the purge cycles of the PSA process. By way of a non-limiting example, control component 40 may adjust the purge flow rate Φp by switching on/off parallel pathways for the gas (e.g., O$_2$) purge flow, by using a proportional valve to vary the purge flow, and/or by other operations. As another non-limiting example, control component 40 may control active (switchable) purge valves 30A and 30B (e.g. electrically operated solenoidal valves) to adjust the purge times (e.g., the time the valves are open), tpA and tpB, to realize the desired adjustments of VpA and VpB.

In some embodiments, control component 40 is configured to cause valves 22 to control the purge cycles of the PSA process based on the different purge volumes of gas determined for sieve beds 12 and 14 to maintain a target purity of the enriched gas for delivery to subject 18. The target purity may be determined by control component 40 based on information from previous therapy sessions for subject 18 or users demographically similar to subject 18, may be determined at manufacture of system 10, may be entered and/or selected via a user interface of system 10 by subject 18 and/or other users, and/or may be determined in other ways.

EXAMPLE

Figure 5:
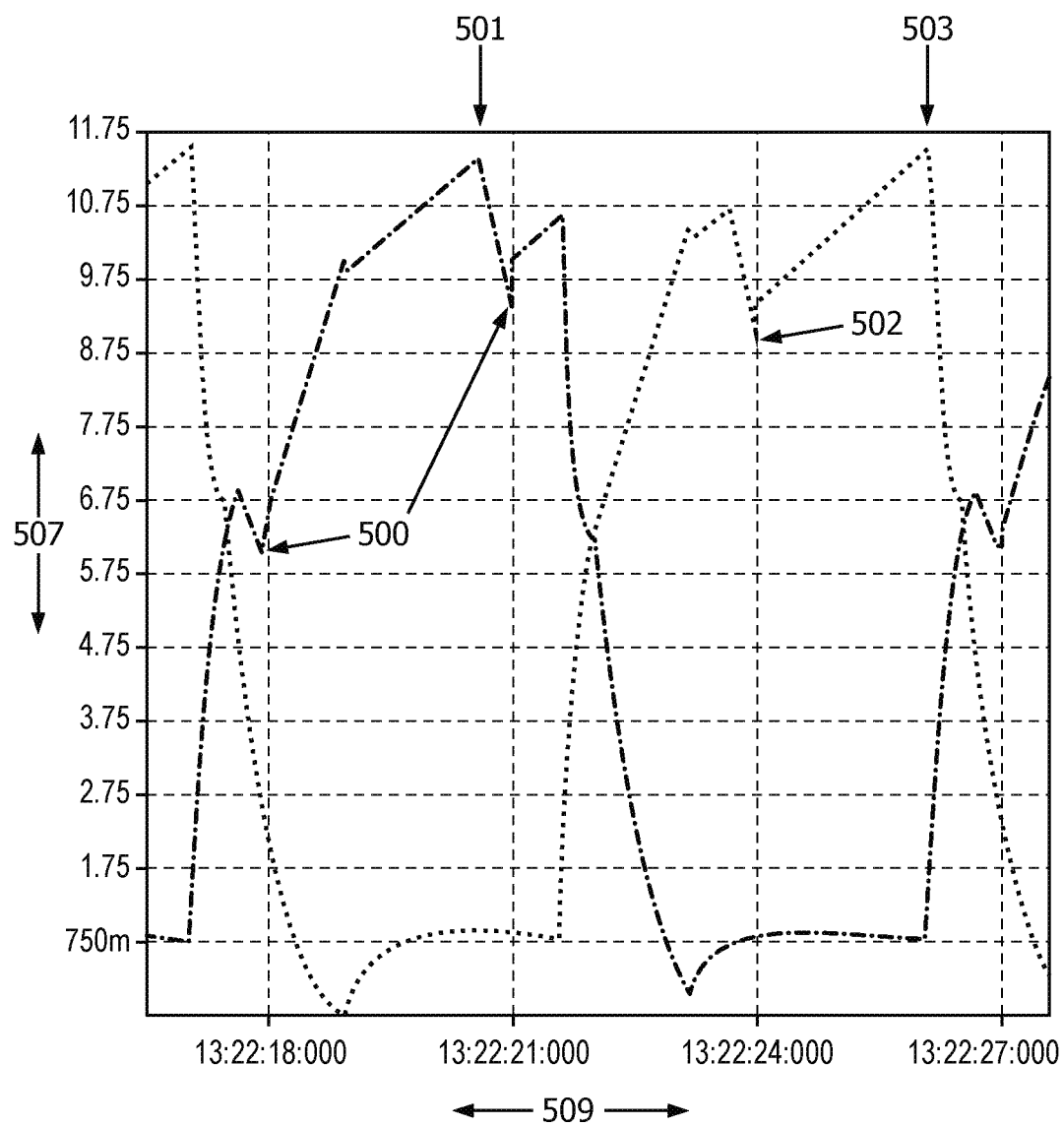
FIG. 5 illustrates pressure traces for boli from two sieve beds, in accordance with one or more embodiments.

Assume system 10 is operated at an O$_2$ product output setting of Φp=0.5 slpm. The cycle time of the POC is $t_{cyc}$=9 s (with a half-cycle time $t_{hcyc}$=4.5 s) and subject 18 is breathing at a constant breathing rate of BR=20 breaths/min. This means that the load condition will be asymmetric with respect to the sieve beds (as described above above). Counting the boli per cycle and per bed reveals that bed 12 is producing 2 boli, whereas bed 14 is producing only 1 bolus per cycle. FIG. 5 illustrates pressure 507 versus time 509 traces 501 and 503 for boli from sieve bed 12 and boli from sieve bed 14 respectively. As shown in FIG. 5, each bolus is reflected by a dip 500 (two dips corresponding to two boli) or 502 (one dip corresponding to one bolus) in the pressure trace for the boli from each bed.

In this example, the target O$_2$ output per cycle per bed is Vt=Φp*$t_{hcyc}$=37.5 smL (smL=standard mL). The Bolus volume is VP=Φp/BR=25 smL. The actual (oxygen) product volumes per cycle are thus VA=2*VP=50 smL and VB=1*VP=25 smL. The O$_2$ product asymmetry is then ΔV=VA−VB=+25 smL. In this asymmetric load condition (and with symmetric purge times tpA=tpB=2.75 s) sieve bed 12 will lose Vt−VA=−12.5 smL of O$_2$ during each cycle, which may lead to N$_2$ breakthrough in sieve bed 12 and poor O$_2$ product purity (≈83% in this example).

To compensate for this load asymmetry, in this example, system 10 (control component 40 shown in FIG. 1A-1D) uses dual purge adjustment compensation and adjusts the purge times tpA and tpB based on a determination of the purge flow Φp through the purge orifice (described above). In this example, the purge flow may described as a flow through an effective orifice, which empirically follows the equation Φp=Φ0*0.0641*(($p_{high}$−$p_{low}$)/psig)^0.537*($p_{low}$/psig+14.5)^0.49. Here, $p_{low}$=pressure at a "lower" end of the orifice, $p_{high}$=pressure at a "high" end of the orifice, and Φ0=an orifice constant [slpm]. The orifice constant Φ0 is proportional to the square of the orifice diameter d such that Φ0 [slpm]=10397*(d [in])$^2$. For an orifice diameter d=0.020 inches, Φ0$_{orifice}$=4.16 slpm. Taking into account that the purge valve and other tubes in series with this orifice will slightly diminish the purge flow, a good estimate for an "effective" purge orifice may be Φ0≈4.0 slpm. From the pressure traces (FIG. 5) control component 40 may determine $p_{high}$ as an average of the "high" sieve pressure during the purge time as $p_{high}$ 10.83 psig, and $p_{low}$ as average of the "low" sieve pressure during the purge time as $p_{low}$≈1.25 psig. Finally, the purge flow Φp will be: Φp=Φ0*0.0641*(($p_{high}$−$p_{low}$)/psig)^0.537*($p_{low}$/psig+14.5)^0.49=3.33 slpm. The theoretical asymmetry of purge times should thus be Δtp=(ΔV/2)/Φp=12.5 smL/3.33 slpm=0.225 s.

Figure 6:
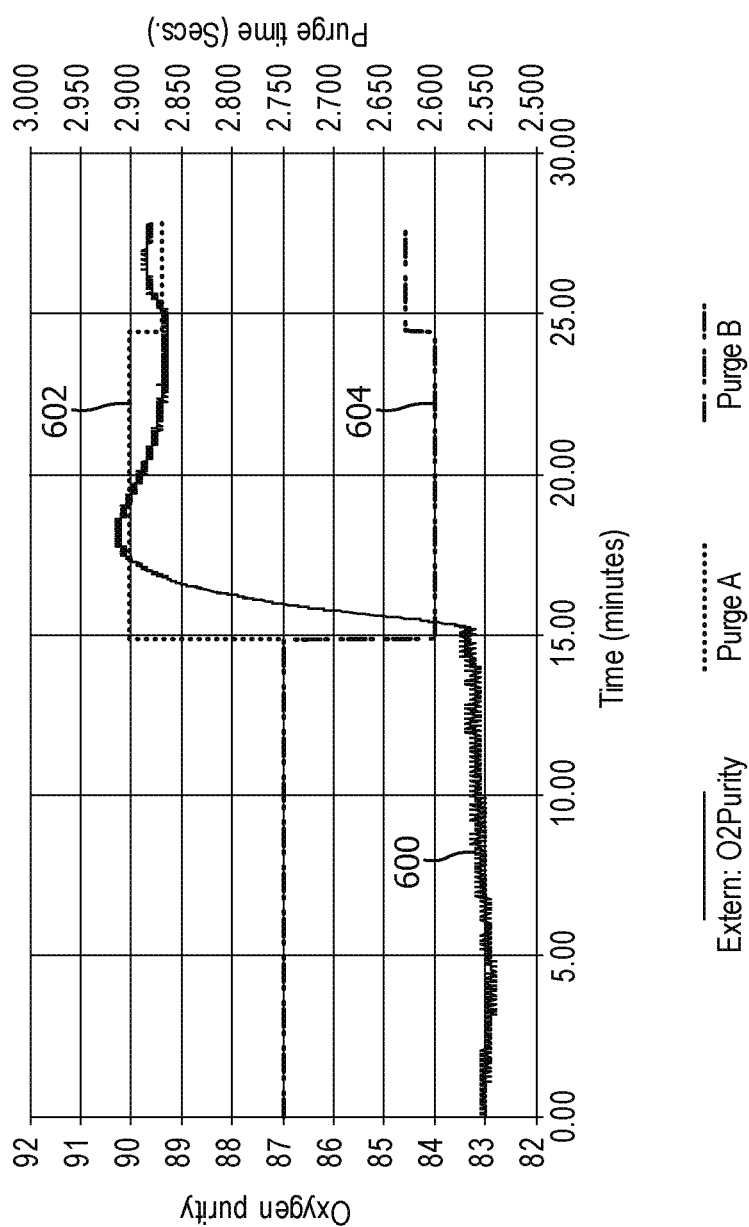
FIG. 6 illustrates average $O_2$ product purity and sieve bed purge times for example operation of the present system, in accordance with one or more embodiments.

FIG. 6 illustrates average O$_2$ product purity 600 and sieve bed purge times tpA 602 and tpB 604 for the example described above (e.g., where system 10 asymmetrically delivers two boli from sieve bed 12 and one bolus from sieve bed 14). As shown in FIG. 6, during the first 15 min gas was delivered to subject 18 (FIG. 1A-1D) the purge times are symmetric (tpA=tpB=2.75 s), and the product purity is low (83.3%). Then the purge volumes (times in this example) are adjusted as described herein to compensate for the asymmetric boli delivery from the different sieve beds (tpA=2.9 s, tpB=2.6 s, which gives Δtp=tpA−tpB=0.30 s). This leads to an increase in (oxygen) product purity (to 90.2%) within the next 3 min. However, product purity then decreases again by about 1%, indicating that the purge volume adjustment (e.g., adjustment of purge times in this example) was too large, over-compensating for the load asymmetry, and bringing sieve bed 14 into a situation of net $O_2$ loss. Finally, FIG. 6 illustrates a second corrective adjustment taken to reduce the previous purge compensation by setting tpA=2.87 s and tpA=2.63 s, which gives Δtp=tpA−tpB=0.24 s. This value is very close to the theoretical value of 0.225 s (see above) and, as a result, the product purity rises again and stabilizes at about 89.6%.

It should be noted that, after the second adjustment, the product purity did not reach the maximum of 90.2%, which had been observed during the previous change of purge times. This is an indication that the optimum setting of purge times is another (small) step away in the same direction. In this way, system 10 (FIG. 1A-1D) may make small adjustments of purge times (for example) to find an optimum setting for purge time, because the theoretical value is just an estimate and not an exact value.

Figure 7:
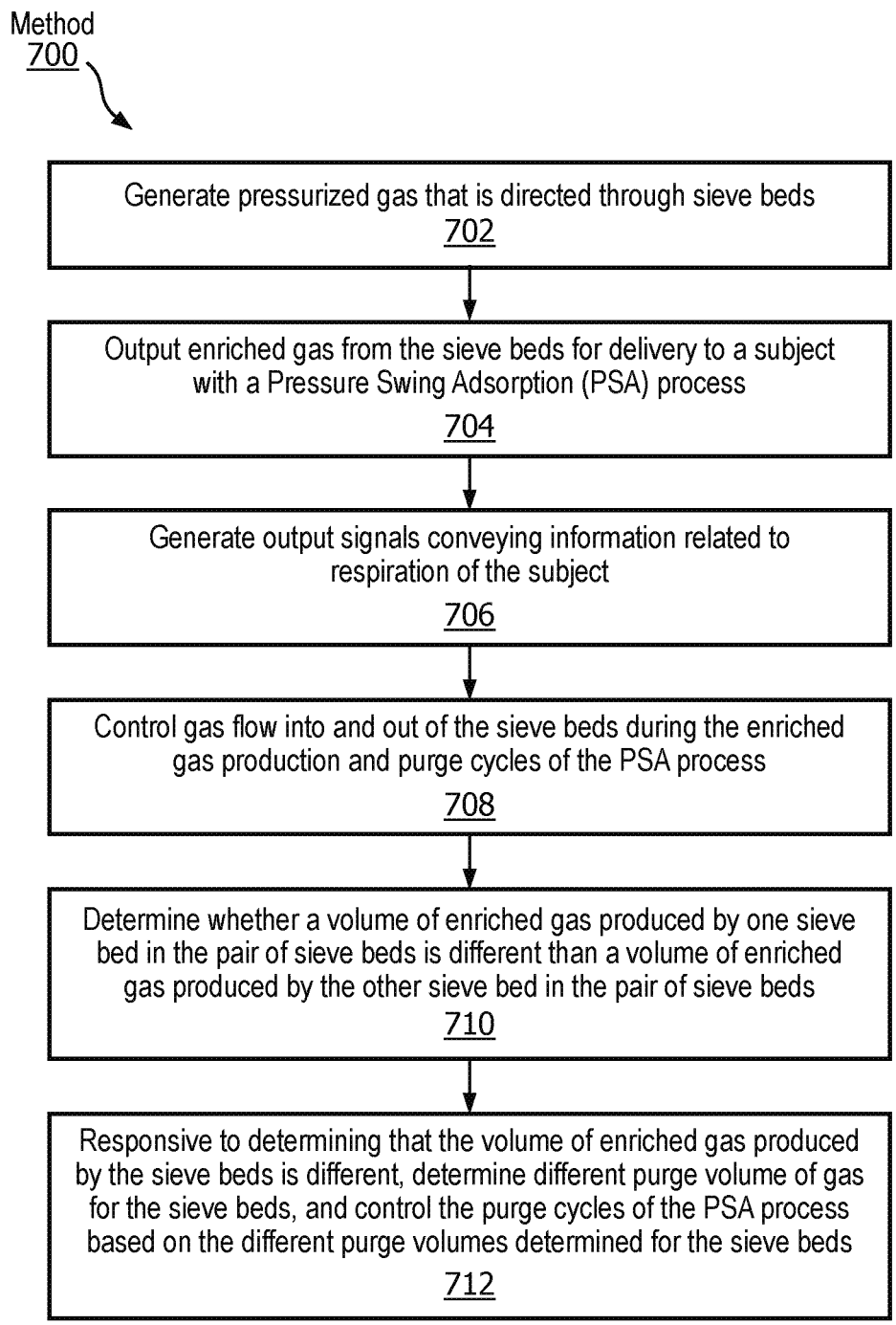
FIG. 7 illustrates a method for concentrating oxygen with a portable oxygen concentration system, in accordance with one or more implementations.

FIG. 7 illustrates a method 700 for concentrating oxygen with a portable oxygen concentration system. The system comprises a pair of sieve beds, a pressure generator, one or more sensors, one or more valves, one or more physical computer processors, and/or other components. The one or more physical computer processors are configured to execute computer program components. The computer program components comprise a control component, an asymmetry component, an adjustment component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, pressurized gas is generated and directed through the sieve beds. In some embodiments, operation 702 is performed by a pressure generator the same as or similar to pressure generator 16 (shown in FIGS. 1A-1D and described herein).

At an operation 704, enriched gas is output from the sieve beds for delivery to a subject with a Pressure Swing Adsorption (PSA) process. The PSA process comprises alternating enriched gas production and purge cycles for each of the sieve beds such that when one of the sieve beds is alternating through an enriched gas production cycle, the other sieve bed is alternating through a purge cycle. In some embodiments, operation 704 is performed by sieve beds the same as or similar to sieve beds 12 and 14 (shown in FIGS. 1A-1D and described herein).

At an operation 706, output signals conveying information related to respiration of the subject are generated. In some embodiments, operation 706 is performed by one or more sensors the same as or similar to sensor 20 (shown in FIGS. 1A-1D and described herein).

At an operation 708, gas flow into and out of the sieve beds is controlled during the enriched gas production and purge cycles of the PSA process. Operation 708 includes causing the valves to control the gas flow into and out of the pair of sieve beds during the enriched gas production and purge cycles of the PSA process based on the output signals. In some embodiments, operation 708 is performed by valves and a processor component the same as or similar to valves 22 and control component 40 (shown in FIGS. 1A-1D and described herein). In some embodiments, the valves comprise two or more feed valves and two or more purge valves, and operation 708 comprises controlling, with the two or more purge valves, gas flow into and out of the pair of sieve beds during the purge cycles of the PSA process.

At an operation 710, a determination of whether a volume of enriched gas produced by one sieve bed in the pair of sieve beds is different than a volume of enriched gas produced by the other sieve bed in the pair of sieve beds is made. Operation 710 includes determining whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds. In some embodiments, determining whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds comprises: (1) counting a number of enriched gas boluses delivered to the subject from each sieve bed, and comparing a count from each sieve bed to each other, or (2) integrating enriched gas bolus flow rates over time for boluses delivered to the subject from each sieve bed to determine a total bolus volume delivered from each sieve bed, and (3) comparing the total bolus volume from each sieve bed to each other. In some embodiments, operation 710 is performed by a processor component the same as or similar to asymmetry component 42 (shown in FIGS. 1A-1D and described herein).

At an operation 712, responsive to determining that the volume of enriched gas produced by the sieve beds is different (e.g., the volume of enriched gas produced by one sieve bed in the pair of sieve beds is different than the volume of enriched gas produced by the other sieve bed in the pair of sieve beds), different purge volumes of gas are determined for the sieve beds, and the purge cycles of the PSA process are controlled based on the different purge volumes determined for the sieve beds. This includes determining different purge volumes of gas for the sieve beds based on the different volumes of enriched gas produced by the sieve beds; and causing the valves to control the purge cycles of the PSA process based on the different purge volumes of gas determined for the sieve beds. In some embodiments, operation 712 includes causing the valves to control the purge cycles of the PSA process based on the different purge volumes of gas determined for the sieve beds to maintain a target purity of the enriched gas for delivery to the subject. In some embodiments, causing the valves to control the purge cycles of the PSA process based on the different purge volumes of gas determined for the sieve beds comprises causing the valves to adjust purge times or flow rates of purge gas during the purge cycles of the PSA process. In some embodiments, causing the valves to control the purge cycles of the PSA process based on the different purge volumes of gas determined for the sieve beds comprises causing the valves to increase or decrease purge times or flow rates of purge gas for one or both sieve beds during the purge cycles of the PSA process such that whichever one of the pair of sieve beds output an increased volume of enriched gas relative to the other sieve bed receives an increased volume of enriched gas relative to the other sieve bed during a purge cycle. In some embodiments, operation 712 is performed by processor components the same as or similar to asymmetry component 42 and control component 40 (shown in FIGS. 1A-1D and described herein).

In some embodiments, operations 710 and 712 include (1) determining whether an amount the volume of enriched gas produced by one sieve bed in the pair of sieve beds is different than the volume of enriched gas produced by the other sieve bed in the pair of sieve beds breaches a volume difference threshold; and responsive to determining that the amount the volume of enriched gas produced by one sieve bed in the pair of sieve beds is different than the volume of enriched gas produced by the other sieve bed in the pair of sieve beds breaches the volume difference threshold: (2) determining the different purge volumes of gas for the sieve beds based on the different volumes of enriched gas produced by the sieve beds; and (3) causing the valves to control the purge cycles of the PSA process based on the different purge volumes of gas determined for the sieve beds.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A portable oxygen concentration system, the system comprising:
   a pair of sieve beds;
   a pressure generator configured to generate pressurized gas that is directed through the sieve beds, wherein the sieve beds output enriched gas for delivery to a subject in a pressure swing adsorption (PSA) process, the PSA process comprising alternating enriched gas production and purge cycles for each of the sieve beds such that when one of the sieve beds is alternating through an enriched gas production cycle, the other sieve bed is alternating through a purge cycle;
   one or more sensors configured to generate output signals conveying information related to respiration of the subject;
   valves configured to control gas flow into and out of the pair of sieve beds during the enriched gas production and purge cycles of the PSA process; and
   one or more processors configured by machine readable instructions to:
      cause the valves to control the gas flow into and out of the pair of sieve beds during the enriched gas production and purge cycles of the PSA process based on the output signals;
      determine whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds; and
      responsive to determining that the volume of enriched gas produced by one sieve bed in the pair of sieve beds is different than the volume of enriched gas produced by the other sieve bed in the pair of sieve beds:
         determine different purge volumes of gas for the sieve beds based on the different volumes of enriched gas produced by the sieve beds; and
         cause the valves to control the purge cycles of the PSA process based on the different purge volumes of gas determined for the sieve beds.

2. The system of claim 1, wherein the one or more processors are further configured to cause the valves to control the purge cycles of the PSA process based on the different purge volumes of gas determined for the sieve beds to maintain a target purity of the enriched gas for delivery to the subject.

3. The system of claim 1, wherein the one or more processors are configured such that causing the valves to control the purge cycles of the PSA process based on the different purge volumes of gas determined for the sieve beds comprises causing the valves to adjust purge times or flow rates of purge gas during the purge cycles of the PSA process.

4. The system of claim 1, wherein the one or more processors are configured such that determining whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds comprises:
   counting a number of enriched gas boluses delivered to the subject from each sieve bed, and comparing a count from each sieve bed to each other, or
   integrating enriched gas bolus flow rates over time for boluses delivered to the subject from each sieve bed to determine a total bolus volume delivered from each sieve bed, and comparing the total bolus volume from each sieve bed to each other.

5. The system of claim 1, wherein the one or more processors are configured such that causing the valves to control the purge cycles of the PSA process based on the different purge volumes of gas determined for the sieve beds comprises causing the valves to increase or decrease purge times or flow rates of purge gas for one or both sieve beds during the purge cycles of the PSA process such that whichever one of the pair of sieve beds output an increased volume of enriched gas relative to the other sieve bed receives an increased volume of enriched gas relative to the other sieve bed during a purge cycle.

6. The system of claim 1, wherein the system does not include a product tank configured to store the enriched gas from the sieve beds.

7. The system of claim 1, wherein the valves comprise two or more feed valves and two or more purge valves, and wherein the two or more purge valves control gas flow into and out of the pair of sieve beds during the purge cycles of the PSA process.

8. The system of claim 1, wherein the one or more processors are further configured to determine whether an amount the volume of enriched gas produced by one sieve bed in the pair of sieve beds is different than the volume of enriched gas produced by the other sieve bed in the pair of sieve beds breaches a volume difference threshold; and
responsive to determining that the amount the volume of enriched gas produced by one sieve bed in the pair of sieve beds is different than the volume of enriched gas produced by the other sieve bed in the pair of sieve beds breaches the volume difference threshold:
determine the different purge volumes of gas for the sieve beds based on the different volumes of enriched gas produced by the sieve beds; and
cause the valves to control the purge cycles of the PSA process based on the different purge volumes of gas determined for the sieve beds.

9. A method for concentrating oxygen with a portable oxygen concentration system, the system comprising a pair of sieve beds, a pressure generator, one or more sensors, one or more valves, and one or more processors, the method comprising:
generating, with the pressure generator, pressurized gas that is directed through the sieve beds;
outputting, with the sieve beds, enriched gas for delivery to a subject from a pressure swing adsorption (PSA) process, the PSA process comprising alternating enriched gas production and purge cycles for each of the sieve beds such that when one of the sieve beds is alternating through an enriched gas production cycle, the other sieve bed is alternating through a purge cycle;
generating, with the one or more sensors, output signals conveying information related to respiration of the subject;
controlling, with the valves, the gas flow into and out of the pair of sieve beds during the enriched gas production and purge cycles of the PSA process;
causing, with the one or more processors, the valves to control the gas flow into and out of the pair of sieve beds during the enriched gas production and purge cycles of the PSA process based on the output signals;
determining, with the one or more processors, whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds;
responsive to determining that the volume of enriched gas produced by one sieve bed in the pair of sieve beds is different than the volume of enriched gas produced by the other sieve bed in the pair of sieve beds:
determining, with the one or more processors, different purge volumes of gas for the sieve beds based on the different volumes of enriched gas produced by the sieve beds; and
causing, with the one or more processors, the valves to control the purge cycles of the PSA process based on the different purge volumes of gas determined for the sieve beds.

10. The method of claim 9, further comprising causing, with the one or more processors, the valves to control the purge cycles of the PSA process based on the different purge volumes of gas determined for the sieve beds to maintain a target purity of the enriched gas for delivery to the subject.

11. The method of claim 9, wherein causing the valves to control the purge cycles of the PSA process based on the different purge volumes of gas determined for the sieve beds comprises causing the valves to adjust purge times or flow rates of purge gas during the purge cycles of the PSA process.

12. The method of claim 9, wherein determining whether causing the valves to control the gas flow into and out of the pair of sieve beds based on the output signals caused a volume of enriched gas produced by one sieve bed in the pair of sieve beds to be different than a volume of enriched gas produced by the other sieve bed in the pair of sieve beds comprises:
counting a number of enriched gas boluses delivered to the subject from each sieve bed, and comparing a count from each sieve bed to each other, or
integrating enriched gas bolus flow rates over time for boluses delivered to the subject from each sieve bed to determine a total bolus volume delivered from each sieve bed, and comparing the total bolus volume from each sieve bed to each other.

13. The method of claim 9, wherein causing the valves to control the purge cycles of the PSA process based on the different purge volumes of gas determined for the sieve beds comprises causing the valves to increase or decrease purge times or flow rates of purge gas for one or both sieve beds during the purge cycles of the PSA process such that whichever one of the pair of sieve beds output an increased volume of enriched gas relative to the other sieve bed receives an increased volume of enriched gas relative to the other sieve bed during a purge cycle.

14. The method of claim 9, wherein the valves comprise two or more feed valves and two or more purge valves, and wherein the method further comprises controlling, with the two or more purge valves, gas flow into and out of the pair of sieve beds during the purge cycles of the PSA process.

15. The method of claim 9, further comprising determining, with the one or more processors, whether an amount the volume of enriched gas produced by one sieve bed in the pair of sieve beds is different than the volume of enriched gas produced by the other sieve bed in the pair of sieve beds breaches a volume difference threshold; and
responsive to determining that the amount the volume of enriched gas produced by one sieve bed in the pair of sieve beds is different than the volume of enriched gas produced by the other sieve bed in the pair of sieve beds breaches the volume difference threshold:

determining, with the one or more processors, the different purge volumes of gas for the sieve beds based on the different volumes of enriched gas produced by the sieve beds; and causing, with the one or more processors, the valves to control the purge cycles of the PSA process based on the different purge volumes of gas determined for the sieve beds.

* * * * *